US012558228B2

(12) United States Patent　　(10) Patent No.:　US 12,558,228 B2

Hales et al.　　(45) Date of Patent:　Feb. 24, 2026

(54) HYDROGEL IMPLANTS FOR MID-FOOT

(71) Applicant: CARTIVA, INC., Alpharetta, GA (US)

(72) Inventors: Richard Clay Hales, Alpharetta, GA (US); Stephanie Marie Mansueti, Atlanta, GA (US)

(73) Assignee: STRYKER CORPORATION, Portage, MI (US)

( * ) Notice: Subject to any disclaimer, the term of this patent is extended or adjusted under 35 U.S.C. 154(b) by 1112 days.

(21) Appl. No.: 17/596,409

(22) PCT Filed: Mar. 30, 2020

(86) PCT No.: PCT/US2020/025724

§ 371 (c)(1),
(2) Date: Dec. 9, 2021

(87) PCT Pub. No.: WO2021/015831

PCT Pub. Date: Jan. 28, 2021

(65) Prior Publication Data

US 2022/0233324 A1　　Jul. 28, 2022

Related U.S. Application Data

(60) Provisional application No. 62/878,504, filed on Jul. 25, 2019.

(51) Int. Cl.
A61F 2/42　　(2006.01)
A61F 2/30　　(2006.01)

(52) U.S. Cl.
CPC ........ *A61F 2/4225* (2013.01); *A61F 2/30767* (2013.01); *A61F 2002/30011* (2013.01); *A61F 2002/30075* (2013.01); *A61F 2002/30168* (2013.01); *A61F 2002/30578* (2013.01); *A61F*

*2002/30934* (2013.01); *A61F 2002/30985* (2013.01); *A61F 2002/4238* (2013.01); *A61F 2310/00023* (2013.01)

(58) Field of Classification Search
CPC ............ A61F 2/4225; A61F 2002/4238; A61F 2002/4228; A61F 2002/4233
See application file for complete search history.

(56) References Cited

U.S. PATENT DOCUMENTS

| | | | |
|---|---|---|---|
| 4,502,161 | A | 3/1985 | Wall |
| 4,936,852 | A | 6/1990 | Kent et al. |
| 6,468,314 | B2 | 10/2002 | Schwartz et al. |
| 7,037,342 | B2 | 5/2006 | Nilsson et al. |
| 7,713,306 | B2 | 5/2010 | Gibbs |
| 8,632,600 | B2 | 1/2014 | Zannis et al. |
| 2002/0022884 | A1 | 2/2002 | Mansmann |

(Continued)

OTHER PUBLICATIONS

First Office Action issued in connection with Chinese Patent Application No. 202080053855.4, Jun. 27, 2024, 8 pages.

(Continued)

*Primary Examiner* — Melanie R Tyson

(74) *Attorney, Agent, or Firm* — DUANE MORRIS LLP

(57)　　　　　　　ABSTRACT

A novel implant for replacing a portion of an articulation surface of a joint is disclosed. The implant includes a bone-engaging surface, a hydrogel portion forming an articulation surface opposite from the first bone-engaging surface, and a bone plate portion configured for securing the implant to a bone that forms the joint.

10 Claims, 21 Drawing Sheets

(56)                     References Cited

U.S. PATENT DOCUMENTS

| 2002/0183845 | A1  | 12/2002 | Mansmann |
| 2004/0199250 | A1  | 10/2004 | Fell |
| 2006/0224244 | A1  | 10/2006 | Thomas et al. |
| 2008/0195211 | A1  | 8/2008 | Lin et al. |
| 2009/0326674 | A1* | 12/2009 | Liu .......................... B22F 3/24 |
| | | | 623/23.55 |
| 2012/0010712 | A1  | 1/2012 | Denoziere et al. |
| 2018/0289493 | A1  | 10/2018 | Mansmann |

OTHER PUBLICATIONS

PCT International Search Report and Written Opinion for PCT/US2020/025724 issued Jul. 15, 2020.
Extended European Search Report issued in connection with European Patent Application No. 20843499.3, 10 pages, Apr. 24, 2023.

* cited by examiner

100

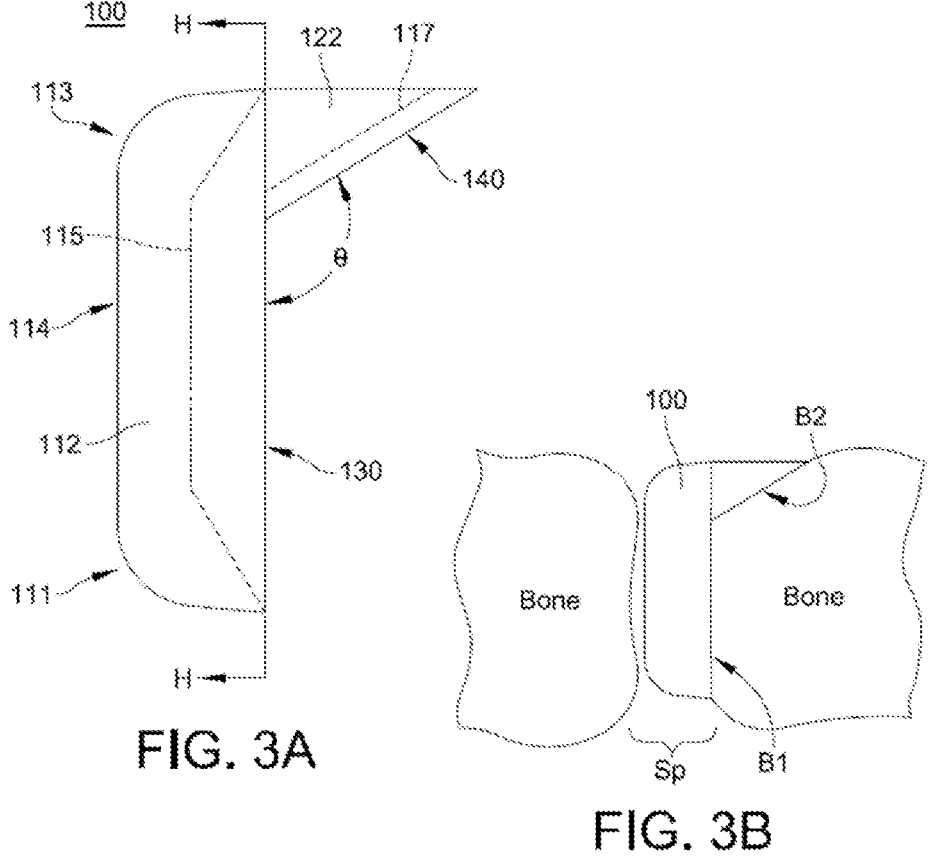
FIG. 3A
FIG. 3B
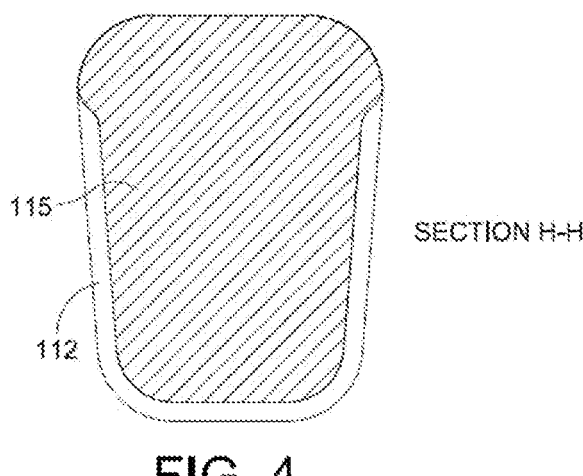
SECTION H-H
FIG. 4

SECTION E-E

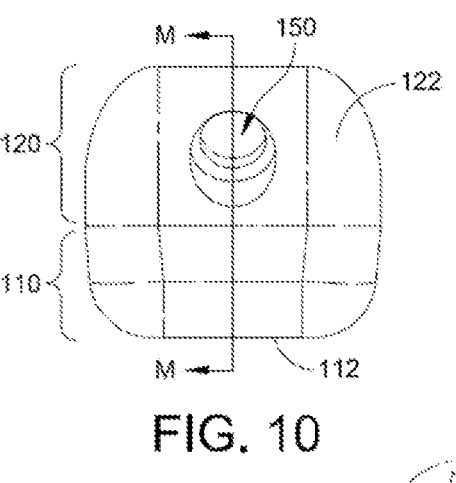
FIG. 10
SECTION M-M
FIG. 11
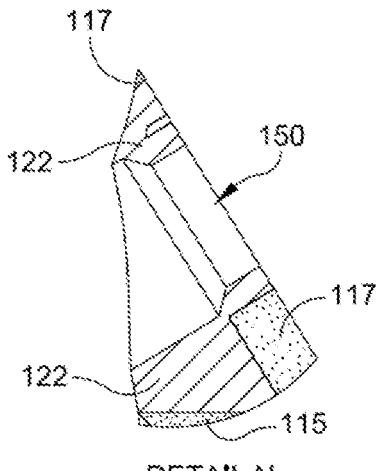
DETAIL N
FIG. 12

225

250

223

SECTION F-F

225

250

DETAIL G

225

227

223

DETAIL N

SECTION C-C

DETAIL E

100A

100A

100A

113A

114A

112A

111A

V

140A

θ

130A

V

100A

116A

SECTION V-V

100
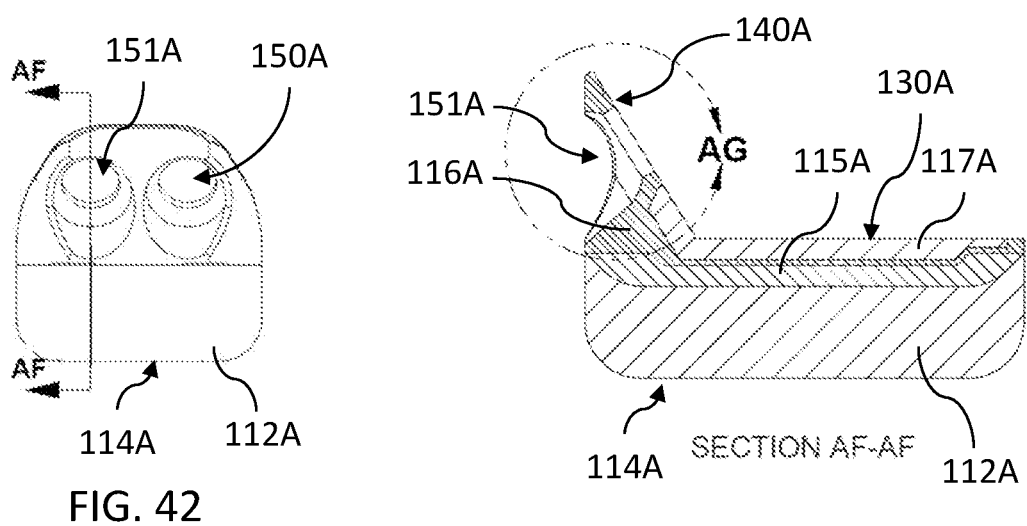
FIG. 42
FIG. 43
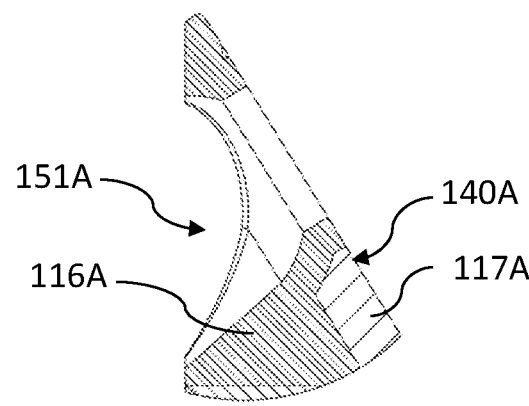
Detail AG
FIG. 44

HYDROGEL IMPLANTS FOR MID-FOOT

This application is a National Stage Application, filed under 35 U.S.C. 371, of International Patent Application No. PCT/US2020/025724, filed on Mar. 30, 2020, which claims the benefit of U.S. Patent Application Ser. No. 62/878,504, filed Jul. 25, 2019, the entireties of which are incorporated herein by reference.

FIELD OF DISCLOSURE

The present disclosure relates generally to orthopedic implants, and more specifically, to hydrogel implants for repairing articulation surfaces in joints in the mid-foot region.

BACKGROUND

Implants can be used to replace deteriorated or otherwise damaged cartilage within a joint. Such devices can be used to treat osteoarthritis, rheumatoid arthritis, other inflammatory diseases, generalized joint pain, and joint damages.

SUMMARY

Disclosed herein is an implant for replacing a portion of an articulation surface of a joint, the implant comprising: a main portion configured for inserting into a joint, wherein the main portion comprises: a porous material portion having a first bone-engaging surface; and a hydrogel portion that is bonded to the porous material portion and forming an articulation surface opposite from the first bone-engaging surface; and a bone plate portion configured for securing the implant to a bone that forms the joint;

wherein, the main portion having a leading end and a trailing end, wherein the leading end is configured for being inserted into the joint;

wherein the bone plate portion is integrally formed with the porous material portion and extends from the trailing end, forming a second bone-engaging surface that is also formed of the porous material and extends from the first bone-engaging surface in a direction opposite from the articulation surface at an angle with respect to the first bone-engaging surface;

wherein the bone plate portion comprises a solid metal portion that forms all exterior surfaces of the bone plate portion except for the second bone-engaging surface; and wherein the bone plate portion has at least one screw hole for receiving a bone screw.

An implant for replacing a portion of an articulation surface of a joint according to another embodiment is disclosed. The implant comprises: a main portion configured for inserting into a joint, wherein the main portion comprises:

a hydrogel portion forming a bone-contacting surface and an articulation surface opposite from the bone-contacting surface;

wherein, the main portion having a leading end and a trailing end, wherein the leading end is configured for being inserted into the joint; and a bone plate portion configured for securing the implant to a bone that forms the joint;

wherein the bone plate portion comprises:

a first part having a perforated structure that is embedded in the hydrogel portion; and a second part that is not embedded in the hydrogel portion and extending from the trailing end in a direction opposite from the articulation surface at an angle ≤160° but ≥80° with respect to the bone-contacting surface;

wherein the second part has at least one screw hole for receiving a bone screw.

An implant for replacing a portion of an articulation surface of a joint according to another embodiment is also disclosed. The implant comprises: a main portion configured for inserting into a joint, wherein the main portion comprises:

a hydrogel portion forming a bone-contacting surface and an articulation surface opposite from the bone-contacting surface;

wherein the bone-contacting surface comprises a protruding part;

wherein, the main portion having a leading end and a trailing end, wherein the leading end is configured for being inserted into the joint; and a bone plate portion configured for securing the implant to a bone that forms the joint; wherein the bone plate portion comprises:

a first part having a perforated structure that is embedded in the protruding part of the hydrogel portion; and a second part that is not embedded in the protruding part of the hydrogel portion and extending from the trailing end in a direction opposite from the articulation surface at an angle ≤160° but ≥80° with respect to the bone-contacting surface;

wherein the second part has at least one screw hole for receiving a bone screw.

An implant for replacing a portion of an articulation surface of a joint according to yet another embodiment is disclosed. The implant comprises: a main portion configured for inserting into a joint and comprising a leading end, a trailing end, an articulation surface and a bone-contacting surface extending between the leading end and the trailing end, wherein the leading end is configured for being inserted into the joint, wherein the main portion further comprises:

a porous material portion; and a hydrogel portion forming the articulation surface and the bone-contacting surface opposite from the articulation surface;

wherein the porous material portion is bonded to the hydrogel portion, extending from the trailing end and partially towards the leading end and forms a portion of the bone-contacting surface;

wherein the porous material portion comprises a tapered hole at the trailing end; and a bone plate configured for securing the implant to a bone that forms the joint;

wherein the bone plate is formed of a solid metal;

wherein the bone plate comprises a tapered stem that is configured to be inserted into the tapered hole in the porous material portion, whereby the tapered stem and the tapered hole cooperate to urge the bone-contacting surface of the implant toward the bone when the implant is inserted into the joint; and wherein the bone plate has at least one screw hole for receiving a bone screw.

The novel implants disclosed herein provides hydrogel implants having hybrid structures that allow repair of articular cartilage surfaces in various joint spaces that were not easily repaired and provide robust and durable repaired surfaces utilizing the benefits of utilizing hydrogel material for articulation surfaces.

BRIEF DESCRIPTION OF THE DRAWINGS

The various embodiments of the inventive hydrogel implant of the present disclosure will be described in more detail in conjunction with the following drawing figures. The structures in the drawing figures are illustrated schematically and are not intended to show actual dimensions.

FIG. 3A is a side view illustration of the hydrogel implant of FIG. 1.

FIG. 3B is a side view illustration of the hydrogel implant of FIG. 1 in implanted position in a joint.

FIG. 4 is a cross-section view illustration of the hydrogel implant of FIG. 1 taken through the section line H-H shown in FIG. 3.

FIG. 10 is a top view illustration of the hydrogel implant of FIG. 1.

FIG. 11 is a cross-section view illustration of the hydrogel implant taken through the section line M-M shown in FIG. 10.

FIG. 12 is a detailed view of the region N identified in the sectional view of FIG. 11.

FIG. 42 is a top view illustration of the hydrogel implant of FIG. 38.

FIG. 43 is a cross-section view illustration of the hydrogel implant taken through the section line AF-AF shown in FIG. 42.

FIG. 44 is a detailed view of the region AG identified in the sectional view of FIG. 43.

DETAILED DESCRIPTION

Figure 1:
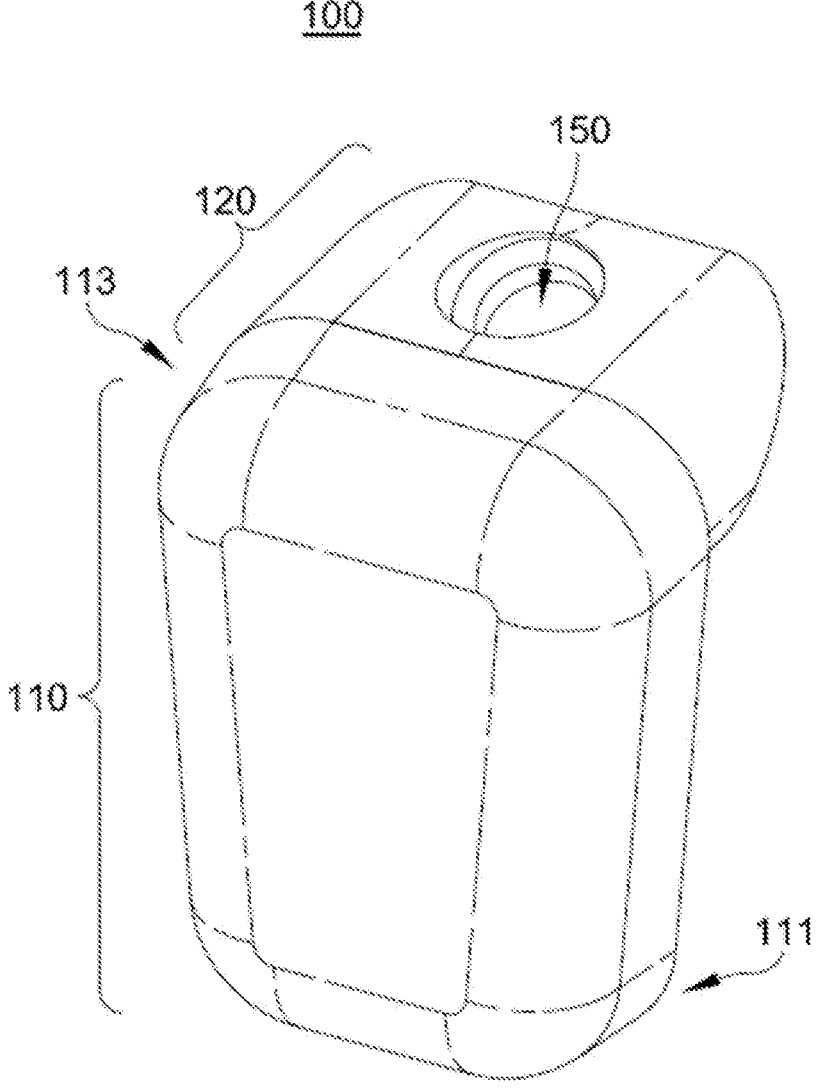
FIG. 1 is a perspective view illustration of a hydrogel implant according to a first embodiment of the present disclosure.

This description of the exemplary embodiments is intended to be read in connection with the accompanying drawings, which are to be considered part of the entire written description. The drawing figures are not necessarily to scale and certain features may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. When only a single machine is illustrated, the term "machine" shall also be taken to include any collection of machines that individually or jointly execute a set (or multiple sets) of instructions to perform any one or more of the methodologies discussed herein. The term "operatively connected" is such an attachment, coupling or connection that allows the pertinent structures to operate as intended by virtue of that relationship. In the claims, means-plus-function clauses, if used, are intended to cover the structures described, suggested, or rendered obvious by the written description or drawings for performing the recited function, including not only structural equivalents but also equivalent structures.

According to an embodiment illustrated in FIGS. 1-12, an implant 100 for replacing a portion of an articulation surface of a joint is disclosed. As shown in FIG. 1, the implant comprises a main portion 110 configured for inserting into a joint and a bone plate portion 120 extending from the main portion 110 at an angle and configured for securing the implant 100 to a bone that forms the joint. As shown in the exploded view of FIG. 2, the main portion 110 comprises a porous material portion 115 having a first bone-engaging surface 130, and a hydrogel portion 112 that is bonded to the porous material portion 115.

Figure 2:
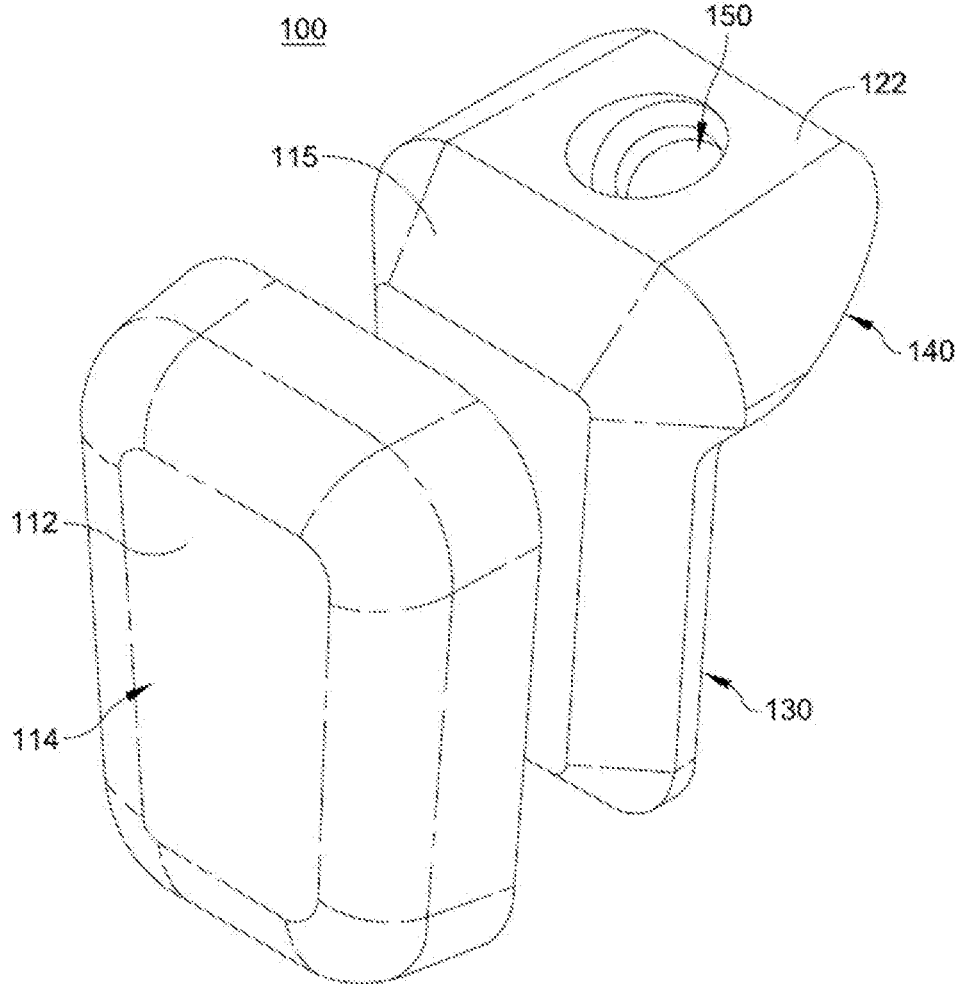
FIG. 2 is an exploded view illustration of the hydrogel implant of FIG. 1.

Referring to FIGS. 2 and 3A, the hydrogel portion 112 forms an articulation surface 114 located opposite from the first bone-engaging surface 130. In other words the articulation surface 114 and the first bone-engaging surface 130 face away from each other. The bone plate portion 120 comprises a solid metal portion 122 that forms all exterior surfaces of the bone plate portion 120 except for the second bone-engaging surface 140. The second bone-engaging surface 140 of the bone plate portion 120 is formed of the same porous material as the porous material portion 115 and is preferably integrally formed with the porous material portion 115 as a unitary structure for ease of manufacturing and producing a more compact structure.

The bone plate portion 120 comprises at least one screw hole 150 for receiving a bone screw that is used to secure the implant 100 to a bone. There can be more than one screw holes provided in the bone plate portion 120 for implanting into a joint repair site that may require more than one bone screw to secure the implant.

The main portion 110 of the implant 100 has a leading end 111 and a trailing end 113, where the leading end is configured for being inserted into the joint. Here, the terms "leading" and "trailing" references generally the implant's orientation in its implanted position in a joint space and also the orientation as the implant is being inserted into the joint space.

The bone plate portion 120 is integrally formed with the porous material portion 115 and extends from the trailing end, forming a second bone-engaging surface 140. Because the extension piece 117 is formed of the same porous material as the porous material portion 115, the second bone-engaging surface 140 also promotes the cancellous bone's growth into the second bone-engaging surface 140 and enhance the implant's stability in the repair site.

As shown by the dashed lines in the side view of the implant 100 in FIG. 3A, the porous material portion 115 has an extension piece 117 that extends from the first bone-engaging surface 130 in a direction opposite from the articulation surface 114 at an angle θ with respect to the first bone-engaging surface 130. The angle θ between the first and second bone-engaging surfaces 130, 140 is selected to enable secure attachment of the implant to the bone. In some embodiments, that angle can be substantially 90°. This means that the angle can be 90°±2°. In some embodiments, the angle is an obtuse angle. In some embodiments, the obtuse angle is ≥110° and ≤160°. In some embodiments, the obtuse angle is ≥130° and ≤140°.

Figure 5:
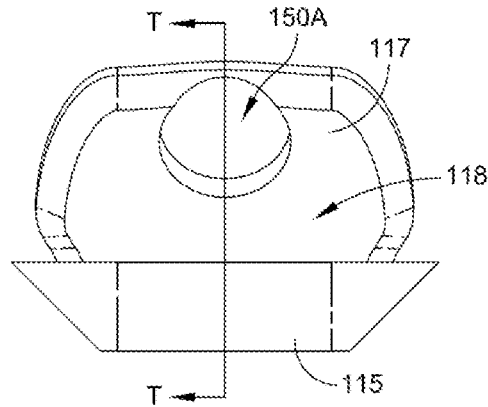
FIG. 5 is a top view illustration of the hydrogel implant of FIG. 1 showing only the porous metal foam portion, i.e., the implant without the hydrogel portion and the solid metal portion.
Figure 6:
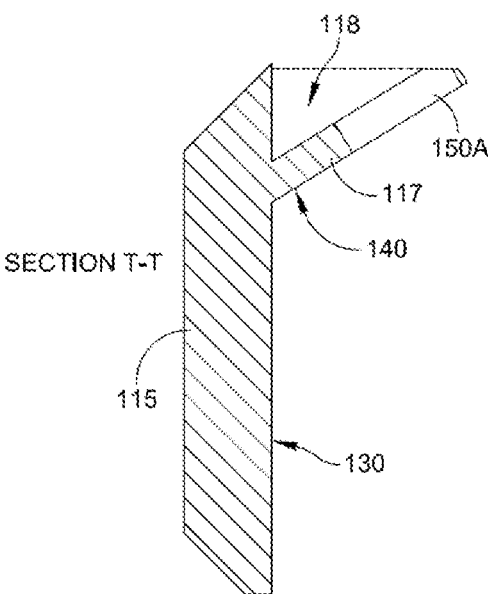
FIG. 6 is a cross-section view illustration of the structure shown in FIG. 5 taken through the section line T-T.
Figures 7, 8, 9:
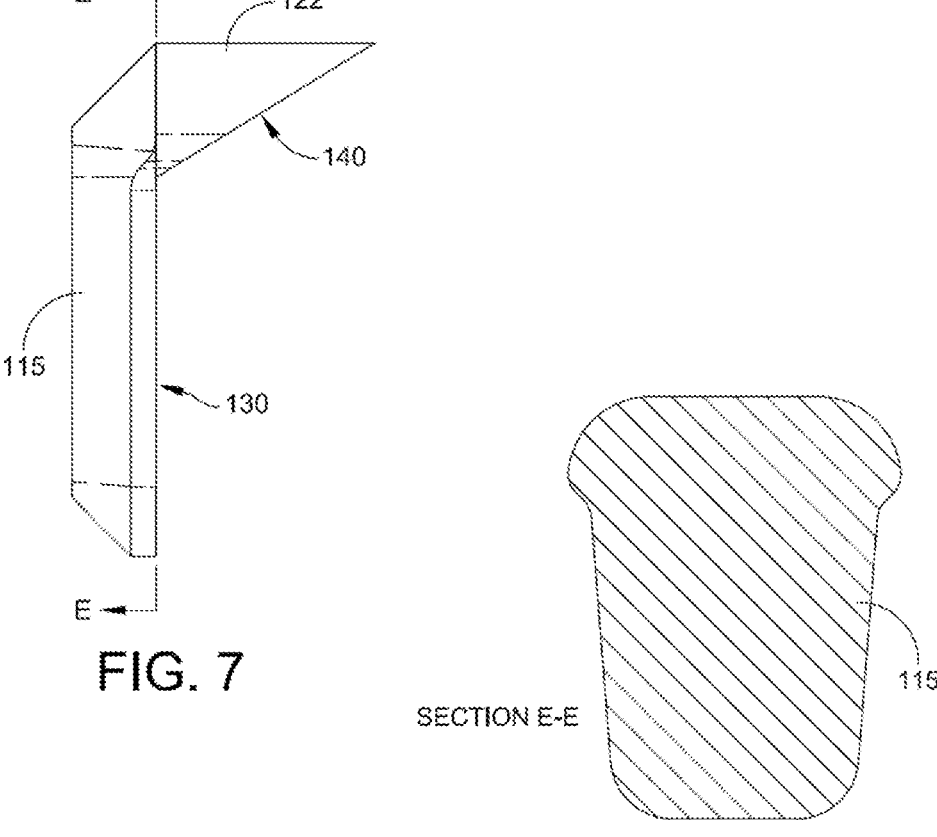
FIG. 7 is a side view illustration of the hydrogel implant of FIG. 1 showing only the porous metal foam and the solid metal portions, i.e., the implant without the hydrogel portion.
FIG. 8 is a cross-section view illustration of the structure shown in FIG. 7 taken through the section line E-E.
FIG. 9 is a top view illustration of the structure shown in FIG. 7.

The extension piece 117 is provided to form the second bone-engaging surface 140. The porous material portion 115 and the extension piece 117 together provide a skeletal base structure on which the hydrogel portion 112 is applied and bonded thereto. This skeletal structure is shown in FIGS. 5 and 6. The solid metal portion 122 fills the space 118 between the extension piece 117 and the porous material portion 115. In some embodiments, the solid metal portion 122 can be integrally formed with the porous material portion 115 and the extension piece 117. FIGS. 7-9 show the porous material structures 115, 117 and the solid metal portion 122 together.

In FIGS. 5 and 6, because only porous material structures 115 and 117 are shown, without the solid metal portion 122, the hole 150A in the extension piece 117 is larger than the bone screw hole 150 which is the final dimension screw hole that is formed by the solid metal portion 122 that overlays on the extension piece 117.

In a preferred embodiment, the porous material structures 115, 117 and the solid metal portion 122 are formed as a unitary structure. For example, the porous material structures and the solid metal portion 122 can be 3-D printed and sintered to form a unitary structure.

In some embodiments, the bone plate portion 120 and the porous material portions 115 and are formed of surgical grade metal. In a preferred embodiment, the surgical grade metal used is titanium. In more preferred embodiment, the solid metal portion 122 is formed of titanium metal and the porous material portion 115 and the extension piece 117 are made of porous titanium metal foam.

The hydrogel portion 112 is bonded to the porous material portion by having some hydrogel material infiltrate into pores of the porous material portion. In preferred embodiments where the porous material is porous titanium metal foam, the hydrogel material infiltrate into pores of the porous titanium metal foam.

The porous material may comprise an oxide material. The porous material can comprise at least one of surgical grade materials such as aluminum, alumina, zirconia, titanium, titania, stainless steel, PEEK, and steatite that are approved for implantation in humans. The porous material can have a porosity between 45 ppi and 80 ppi. Pores of the porous material can have a dimension between 100 μm and 500 μm. The porous material can be ceramic, metal, or plastic. In some embodiments, the porous material comprises porous ceramic material (e.g., oxide-ceramic), metal (e.g., titanium (e.g., titanium mesh, printed titanium), stainless steel (e.g., stainless steel wool), plastic (e.g., polyaryl ether ketone (PAEK) (e.g., polyether ether ketone (PEEK)), other biocompatible materials, combinations thereof, etc.) In some preferred embodiments, the porous material is porous metal foam material that has open-celled three-dimensional scaffold structure for bone and tissue growth.

In more preferred embodiments, the porous metal foam material is porous titanium foam. An example of such porous titanium foam material is Wright Medical Technology's BIOFOAM® Cancellous Titanium™ technology. The titanium matrix of BIOFOAM® Cancellous Titanium™ technology has fully interconnected porosity of up to 70% providing an ideal environment for optimum bone ingrowth and incorporation. The titanium matrix of BIOFOAM® Cancellous Titanium™ technology has: compressive strength that is between that of cortical and cancellous bone, thus minimizing deformation under dynamic loading conditions; compressive modulus that is close to that of cancellous bone, allowing the natural transfer of dynamic loads away from the implant to the surrounding bone; and high surface coefficient of friction that provides initial stability in the interface between the implant and the bone, minimizing micro motion and creating a stable environment for rapid ingrowth and fixation. Examples of alternative materials for the porous metal foam is titanium dioxide foam and porous tantalum foam.

Referring to FIG. 3B, when the implant 100 is implanted in a patient to repair or replace a portion of an articulation surface (e.g., articular cartilage) in a joint, the damaged articulation surface and the adjacent bone region would be prepared to receive the implant 100. The prepared site would have resected bone surfaces B1 and B2 corresponding to the first bone-engaging surface 130 and the second bone-engaging surface 140 of the implant 100. All or much of the resected bone surfaces B1 and B2 would generally be comprised of cancellous bone and because the first and second bone-engaging surfaces 130, 140 are formed of porous metal foam material that has a mesh-like structure with many pores mimicking the cancellous bone structure, the cancellous bone grows into the porous metal foam structure and further enhances the securement of the implant 100 in the repair site.

The hydrogel portion 112 can be formed by applying the hydrogel material in a liquid form on the porous material structure 115 in a mold and then allowing the hydrogel material to cross-link by conducting the appropriate processes that are appropriate for the particular type of hydrogel material that is selected for a given application for the implant.

In some embodiments of the implant 100, the bond between the hydrogel portion and the porous material portion is enhanced by having some hydrogel material infiltrating into the pores in a portion of the porous material along the surface that comes in contact with the hydrogel material. Thus, in a region in the porous material structure 115 along the hydrogel portion 112, both the hydrogel material and the porous material co-exist while in the remainder of the porous material structure 115 toward the bone-engaging surface 130, only the porous material exists without any hydrogel material. That allows the bone-engaging surface 130 to present pores that enable cancellous bone ingrowth.

The hydrogel material referred to herein refers to a three-dimensional solid resulting from cross-linked hydrophilic polymer chains formed of polyvinyl alcohol (PVA). The hydrogel material can comprise one or more other materials in addition to PVA, such as, for example, other hydrogels, other polymeric materials, additives, and/or the like. In some embodiments, the PVA content of the hydrogel in the implants disclosed herein can be about 40% by weight. The PVA content of the hydrogel can range from about 10% by weight to about 80% by weight, as appropriate for particular application.

The hydrogel can comprise water, saline, other liquids, combinations thereof, and/or the like. In some embodiments, saline may be preferred over water, because, under certain circumstances, saline can help maintain osmotic balance with surrounding anatomical tissues following implantation. The exact composition of the hydrogel component in an implant can be selected for optimal performance in a particular application to achieve the desired or required strength, load bearing capacity, compressibility, flexibility, longevity, durability, resilience, coefficient of friction, and/or other properties and characteristics.

In some embodiments, such hydrogel portions of the implants can be formulated for drug delivery and/or is seeded with growth factors and/or cells. In such embodiments, the hydrogel component can comprise one or more of the following: chondrocytes, growth factors, bone morphogenetic proteins, collagen, hyaluronic acid, nucleic acids, and stem cells. Such factors and/or any other materials included in the implants can help facilitate and/or promote long-term fixation of the implants at the joint site.

FIG. 10 shows a top view illustration of the hydrogel implant 100. FIG. 11 is a cross-section view illustration of the hydrogel implant 100 taken through the section line M-M shown in FIG. 10. FIG. 12 is a detailed view of the region N identified in the sectional view of FIG. 11.

Figure 38:
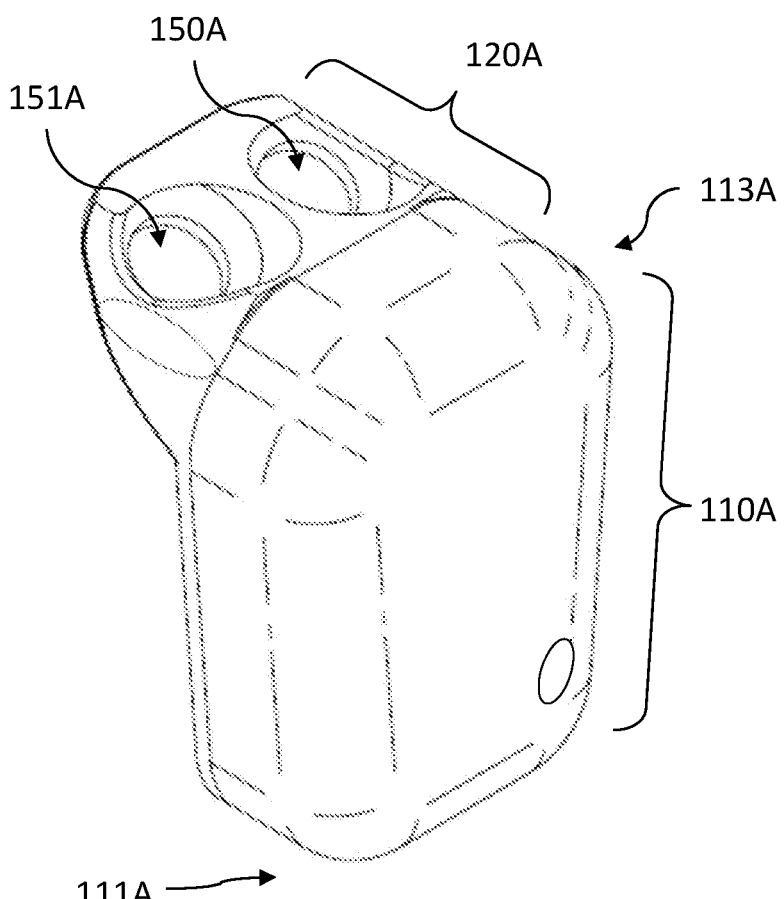
FIG. 38 is a perspective view illustration of a hydrogel implant according to another embodiment of the present disclosure.

Referring to FIGS. 38-41, an implant 100A for replacing a portion of an articulation surface of a joint according to another embodiment is disclosed. As shown in FIG. 38, the implant comprises a main portion 110A configured for inserting into a joint and a bone plate portion 120A extending from the main portion 110A at an angle and configured for securing the implant 100A to a bone that forms the joint. As shown in the exploded view of FIG. 39, the implant 100A comprises four different components that are bonded together in the following order: a first porous material portion 117A, a solid metal portion 116A, a second porous material portion 115A, and a hydrogel portion 112A.

Figure 39:
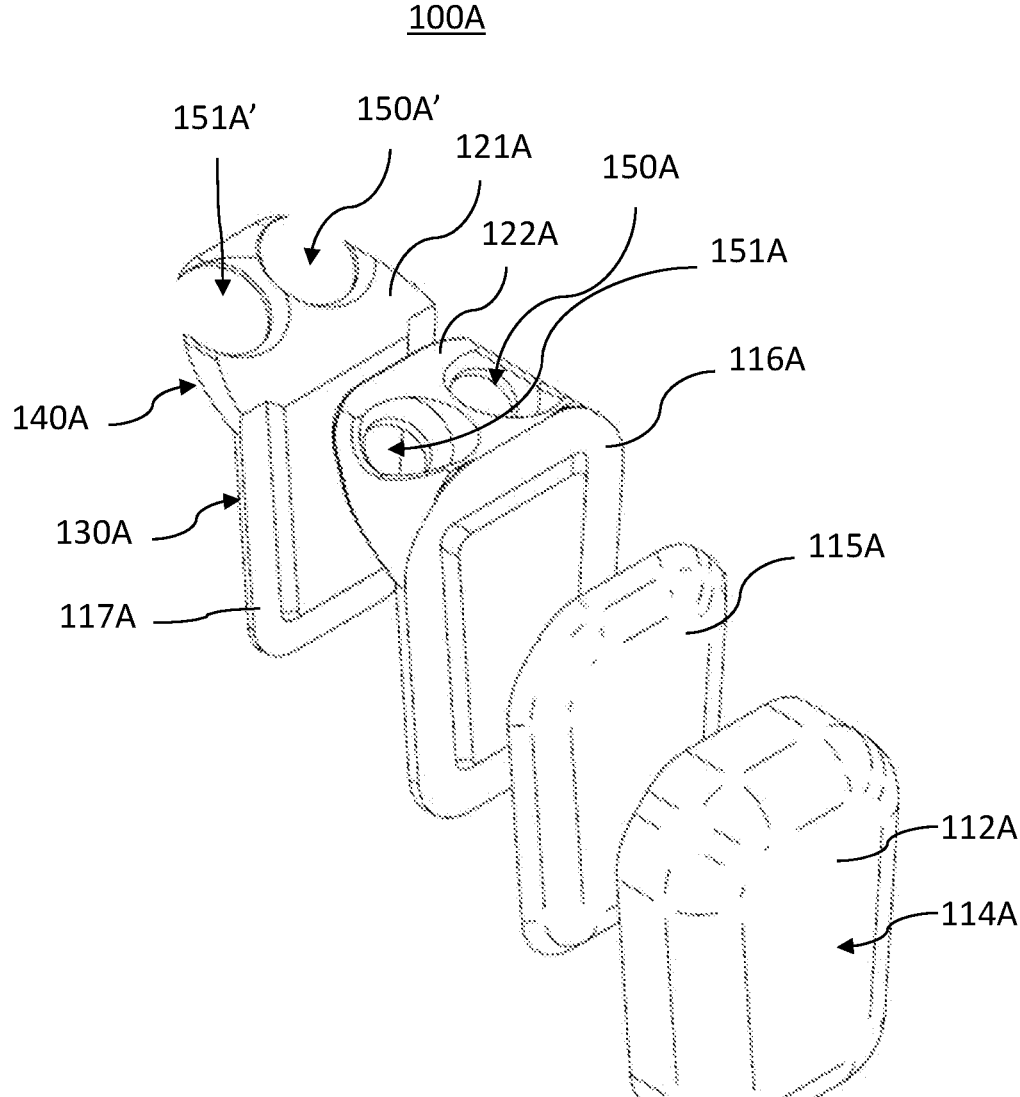
FIG. 39 is an exploded view illustration of the hydrogel implant of FIG. 38.
Figures 40, 41:
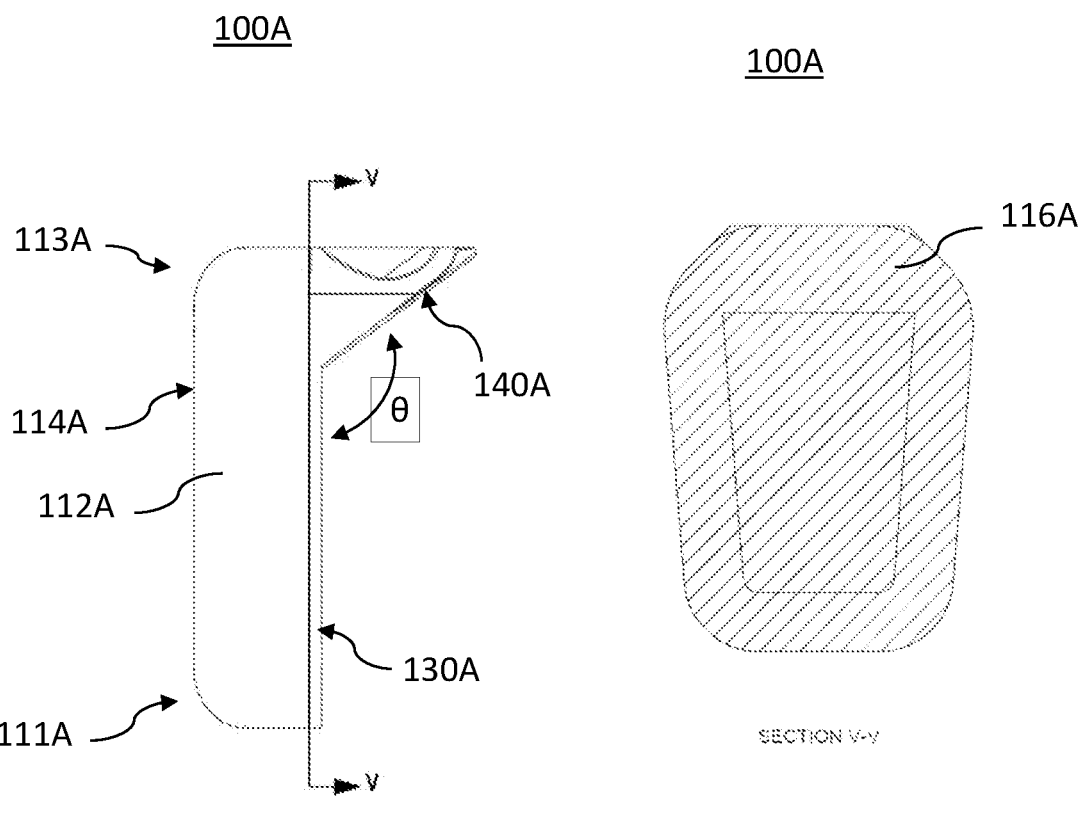
FIG. 40 is a side view illustration of the hydrogel implant of FIG. 38.
FIG. 41 is a cross-section view illustration of the hydrogel implant of FIG. 38 taken through the section line V-V shown in FIG. 40.

Referring to FIGS. 39 and 40, which is a side view of the implant 100A, the first porous material portion 117A has a first bone-engaging surface 130A, and a second bone-engaging surface 140A. The top portion 121A of the first porous material portion 117A form the second bone-engaging surface 140A and the remaining portion of the first porous material portion 117A form the first bone-engaging surface 130A. On the side opposite of the two bone-engaging surfaces 130A, 140A, the solid metal portion 116A is bonded to the first porous material portion 117A.

The solid metal portion 116A comprises a top portion 122A, which together with the top portion 121A of the first porous material portion 117A form the bone plate portion 120A of the implant 100A. Similar to the implant 100 described above, the bone plate portion 120A of the implant 100A also comprises at least one screw hole for receiving a bone screw that is used to secure the implant 100A to a bone. In the illustrated example shown, two screw holes 150A and 151A are provided in the bone plate portion 120A for implanting into a joint repair site that may require more than one bone screw to secure the implant. The top portion 121A of the first porous material portion 117A comprises holes 150A' and 151A' that correspond to the two screw holes 150A and 151A.

The top portion 122A of the solid metal portion 116A forms the exterior surface of the bone plate portion 120A while the second bone-engaging surface 140A is formed by the first porous material portion 117A.

The second porous material portion 115A is positioned between and bonded to both the solid metal portion 116A and the hydrogel portion 112A. The hydrogel portion 112A forms an articulation surface 114A located opposite from the first bone-engaging surface 130A. In other words, the articulation surface 114A and the first bone-engaging surface 130A face away from each other.

The main portion 110A of the implant 100A has a leading end 111A and a trailing end 113A, where the leading end 111A is configured for being inserted into the joint. Here, the terms "leading" and "trailing" references generally the implant's orientation in its implanted position in a joint space and also the orientation as the implant is being inserted into the joint space.

Both the first and second porous material portions 117A and 115A are preferably made of the same porous material. The first porous material portion 117A which forms the first and second bone-engaging surfaces, 130A and 140A, respectively, promotes the cancellous bone's growth into the bone-engaging surfaces 130A, 140A and enhance the implant's stability in the repair site.

As shown in FIG. 40, the first bone-engaging surface 130A is substantially parallel to the articulation surface 114A of the hydrogel portion 112A. The second bone-engaging surface 140A of the bone plane portion 120A and the first bone-engaging surface 130A form an angle θ with respect to the first bone-engaging surface 130. The angle θ between the first and second bone-engaging surfaces 130A, 140A is selected to enable secure attachment of the implant to the bone. In some embodiments, that angle can be substantially 90°. This means that the angle can be 90°±2°. In some embodiments, the angle is an obtuse angle. In some embodiments, the obtuse angle is ≥110° and ≤160°. In some embodiments, the obtuse angle is ≥130° and ≤140°.

The first porous material portion 117A, the solid metal portion 116A, and the second porous material portion 115A together provide a skeletal base structure on which the hydrogel portion 112A is applied and bonded thereto. In some embodiments, the solid metal portion 116A can be integrally formed with the first and second porous material portions 117A and 115A as a unitary structure. For example, the porous material structures and the solid metal portion 116A can be 3-D printed and sintered to form a unitary structure.

As in the implant embodiment 100, the solid metal portion 116A and the porous material portions 117A, 115A can be formed of surgical grade metal such as titanium and/or titanium alloys.

The hydrogel portion 112A is bonded to the second porous material portion 115A by having some hydrogel material infiltrate into pores of the porous material portion. In preferred embodiments where the porous material is porous titanium metal foam, the hydrogel material infiltrate into pores of the porous titanium metal foam. The porous material may comprise of the materials described above in connection with the implant 100.

When implanted in a patient, the implant 100A's arrangement will be similar to the example for implant 100 shown in FIG. 3B.

The hydrogel portion 112A can be formed by applying the hydrogel material in a liquid form on the porous material structure 115A in a mold and then allowing the hydrogel material to cross-link by conducting the appropriate processes that are appropriate for the particular type of hydrogel material that is selected for a given application for the implant.

In some embodiments of the implant, the bond between the hydrogel portion and the porous material portion is enhanced by having some hydrogel material infiltrating into the pores in a portion of the porous material along the surface that comes in contact with the hydrogel material. Thus, in a region in the porous material structure 115A along the hydrogel portion 112A, both the hydrogel material and the porous material co-exist while in the remainder of the porous material structure 115A toward the bone-engaging surface 130A, only the porous material exists without any hydrogel material. That allows the bone-engaging surface 130A to present pores that enable cancellous bone ingrowth.

FIG. 42 is a top view illustration of the hydrogel implant 100A. FIG. 43 is a cross-section view illustration of the hydrogel implant 100A taken through the section line AF-AF shown in FIG. 42. FIG. 44 is a detailed view of the region AG identified in the sectional view of FIG. 43.

Figure 13:
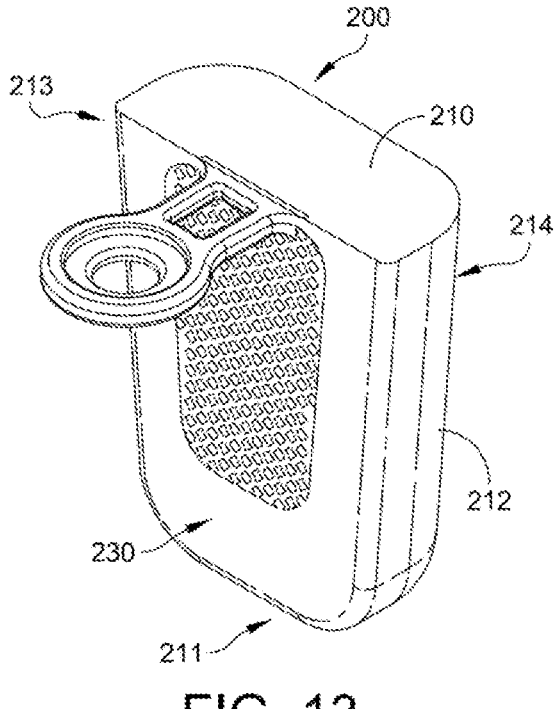
FIG. 13 is a perspective view of a hydrogel implant according to a second embodiment.
Figure 14:
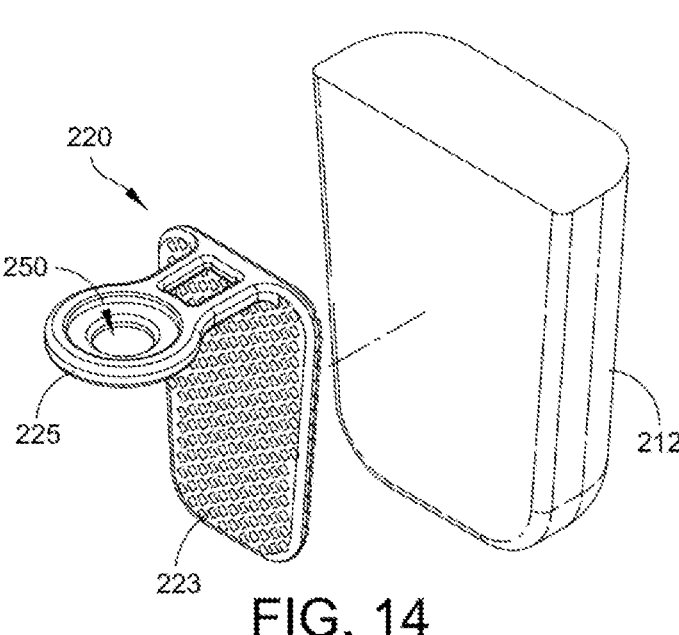
FIG. 14 is an exploded view illustration of the hydrogel implant of FIG. 13.
Figure 15:
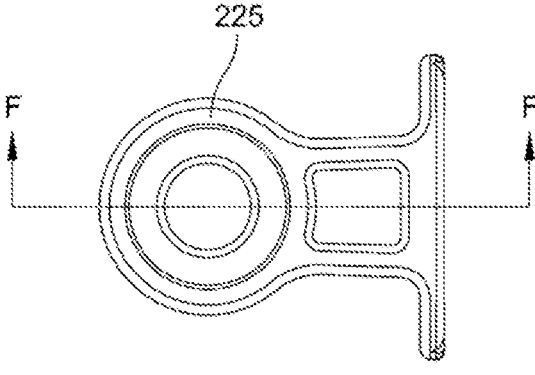
FIG. 15 is a top view of the bone plate portion of the hydrogel implant of FIG. 13.
Figure 16:
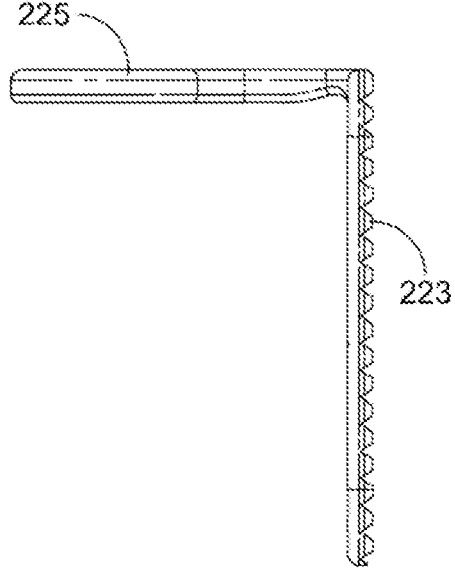
FIG. 16 is a side view of the bone plate portion shown in FIG. 15.
Figure 17:
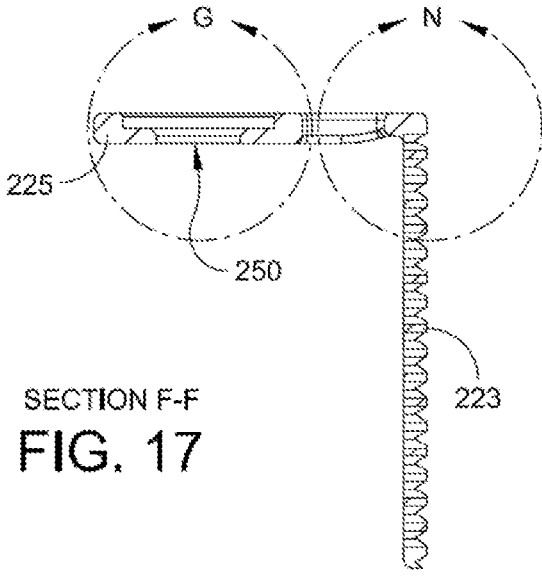
FIG. 17 is a cross-section view of the bone plate portion taken through the section line F-F shown in FIG. 15.
Figure 18:
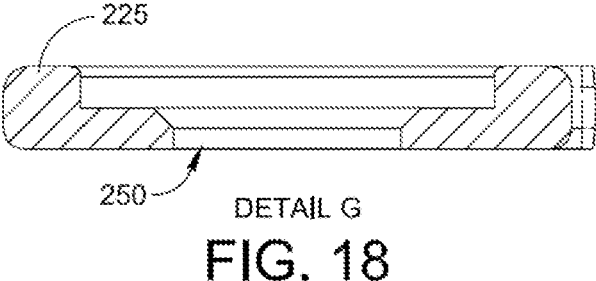
FIG. 18 is a detailed view of the region G identified in the sectional view of FIG. 17.

Referring to FIGS. 13-19, an implant 200 for replacing a portion of an articulation surface of a joint according to another embodiment is disclosed. The implant 200 comprises a main portion 210 configured for inserting into a joint. The main portion 210 can comprise a hydrogel portion 212 forming a bone-contacting surface 230 and an articulation surface 214 opposite from the bone-contacting surface 230. The main portion 210 has a leading end 211 and a trailing end 213, wherein the leading end is configured for being inserted into the joint. A bone plate portion 220 configured for securing the implant 200 to a bone that forms the joint. The bone plate portion 220 comprises a first part 223 having a perforated structure that is embedded in the hydrogel portion 212; and a second part 225 that is not embedded in the hydrogel portion and extending from the trailing end 213 in a direction opposite from the articulation surface 214 at an angle ≤160° but ≥80° with respect to the bone-contacting surface 230. The second part 225 has at least one screw hole 250 for receiving a bone screw (not shown). The second part 225 can have generally circular configuration around the screw hole 250 as shown in FIG. 15, but the shape of the second part 225 can be designed to have any appropriate shape to fit into the structure (e.g. contour) of the bones around the particular joint space into which the implant 200 will be implanted.

In some embodiments of the implant 200, the second part 225 extends from the trailing end 213 at an angle that is ≤110° and ≥80°. In some embodiments of the implant 200, the second part 225 extends from the trailing end 213 at an angle that is substantially 90° (i.e., 90±2°). In some embodiments of the implant 200, the first part 223 of the bone plate portion 220 is embedded in the hydrogel portion 212 and located closer to the bone-contacting surface 230 than the articulation surface 214. In some embodiments of the implant 200, the bone-contacting surface 230 is a flat surface. When the bone-contacting surface 230 is a flat surface, the first part 223 of the bone plate portion 220 has substantially flat configuration as shown in FIGS. 13 and 14 to correspond to the flat contour of the bone-contacting surface 230.

Figure 19:
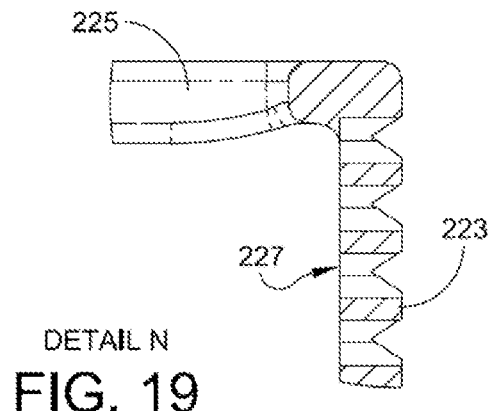
FIG. 19 is a detailed view of the region N identified in the sectional view of FIG. 17.
Figure 20:
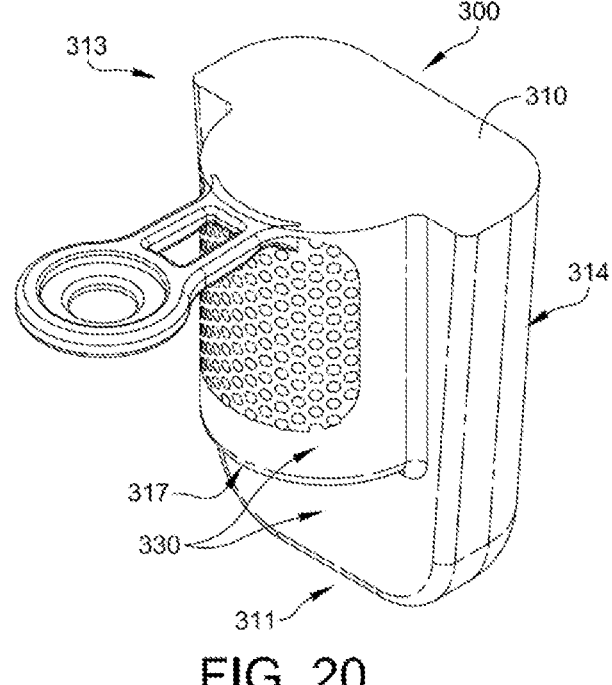
FIG. 20 is a perspective view of a hydrogel implant according to a third embodiment.

The implant 200 can be formed by molding the hydrogel material around the first part 223 of the bone plate portion 220 using injection molding or open cavity molding processes known to those in the art. As shown in FIGS. 14 and 19, the first part 223 of the bone plate portion 220, the part that gets embedded in the hydrogel portion 212, can be perforated with holes 227 to better enable the hydrogel material to intimately surround and envelope the first part 223 during the molding process so that the resulting implant 200 has the optimal structural integrity.

The bone plate portion 220 is made of a surgical grade metal, such as stainless steel, cobalt based superalloys, titanium, titanium alloys, etc. In some embodiments, the surgical grade metal is titanium.

Referring to FIGS. 20-24, an implant 300 according to another embodiment is disclosed. The implant 300 is similar to the implant 200 just described with one of the differences being the provision of a protruding part 316 on the bone-contacting surface 330.

The implant 300 for replacing a portion of an articulation surface of a joint comprises a main portion 310 configured for inserting into a joint. The main portion 310 comprises a hydrogel portion 312 forming a bone-contacting surface 330 and an articulation surface 314 opposite from the bone-contacting surface 330. The bone-contacting surface 330 comprises the protruding part 316 that provides additional structural stability at the interface between the bone and the bone-contacting surface 330 when the implant 300 is implanted in position in a joint space. Preferably, the bone surface that is receiving the implant 300 would be prepared to have a contour that is complementary to the contour of the bone-contacting surface 330 that includes the protruding part 316.

Figure 21:
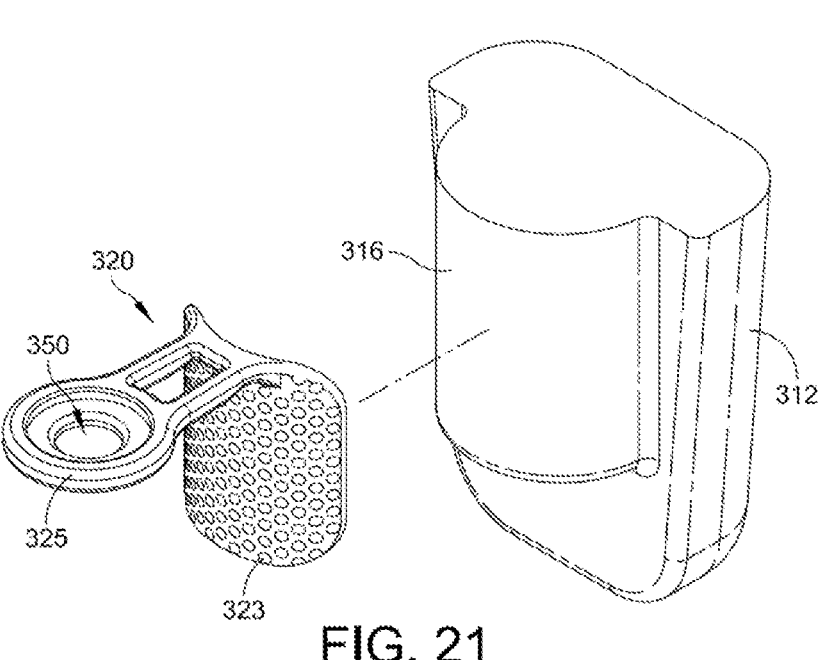
FIG. 21 is an exploded view illustration of the hydrogel implant of FIG. 20.
Figure 22:
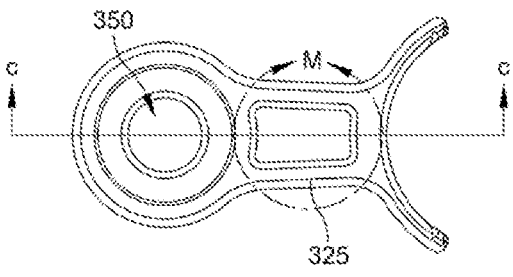
FIG. 22 is a top view of the bone plate portion of the hydrogel implant of FIG. 20.
Figure 23:
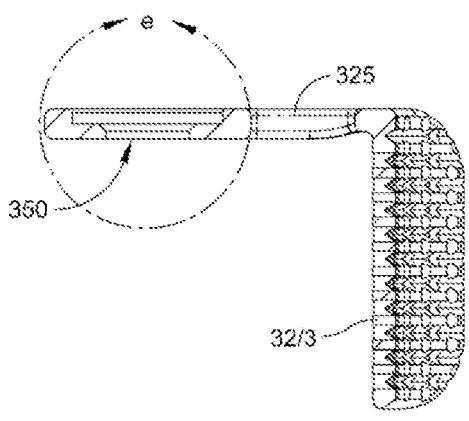
FIG. 23 is a cross-section view of the bone plate portion taken through the section line C-C shown in FIG. 22.
Figure 24:
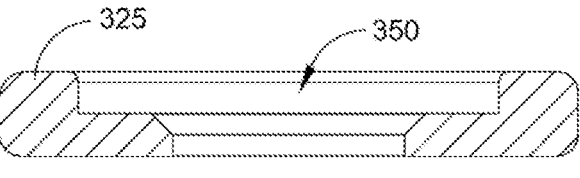
FIG. 24 is a detailed view of the region E identified in the sectional view of FIG. 23.

Similar to the implant 200, the main portion 310 of the implant 300 comprises a leading end 311 and a trailing end 313, where the leading end 311 is configured for being inserted into the joint. The implant 300 further comprises a bone plate portion 320 configured for securing the implant 300 to a bone that forms the joint. The bone plate portion 320 comprises a first part 323 having a perforated structure that is embedded in the protruding part 316 of the hydrogel portion 312, and a second part 325 that is not embedded in the protruding part of the hydrogel portion. The second part 325 extends from the trailing end 313 in a direction opposite from the articulation surface 314 at an angle ≤160° but ≥80° with respect to the base flat portion of the bone-contacting surface 330 (i.e., the part of the bone-contacting surface 330 excluding the protruding part 316. The second part has at least one screw hole 350 for receiving a bone screw (not shown). Similar to the implant 200, the second part 325 can have generally circular configuration around the screw hole 350 as shown in FIG. 21, but the shape of the second part 325 can be designed to have any appropriate shape to fit into the structure (e.g. contour) of the bones around the particular joint space into which the implant 300 will be implanted.

In some embodiments of the implant 300, the second part 325 extends from the trailing end 313 at an angle that is ≤110° and ≥80°. In some embodiments of the implant 300, the second part 325 extends from the trailing end 313 at an angle that is substantially 90° (i.e., 90±2°). In some embodiments, the first part 323 of the bone plate portion is embedded in the hydrogel portion and located closer to the bone-contacting surface 330 than the articulation surface 314. Preferably, the first part 323 of the bone plate portion 320 has a contour that substantially matches the contour of the protruding part 316 of the hydrogel portion 312.

In some embodiments, the protruding part 316 of the bone-contacting surface 330 has a half-cylinder contour and the first part 323 of the bone plate portion has a complementary curved contour. In some embodiments of the implant 300, the bone plate portion 320 is made of a surgical grade metal, such as stainless steel, cobalt based superalloys, titanium, titanium alloys, etc. In some embodiments, the surgical grade metal is titanium.

Figure 25:
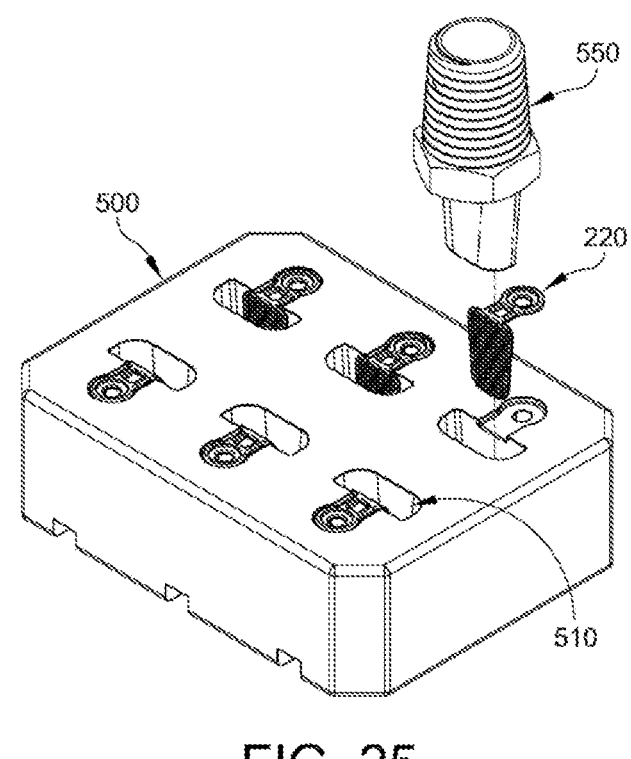
FIG. 25 is an illustration of an example of a mold that can be used to form the hydrogel implants of the present disclosure by injection molding.
Figure 26:
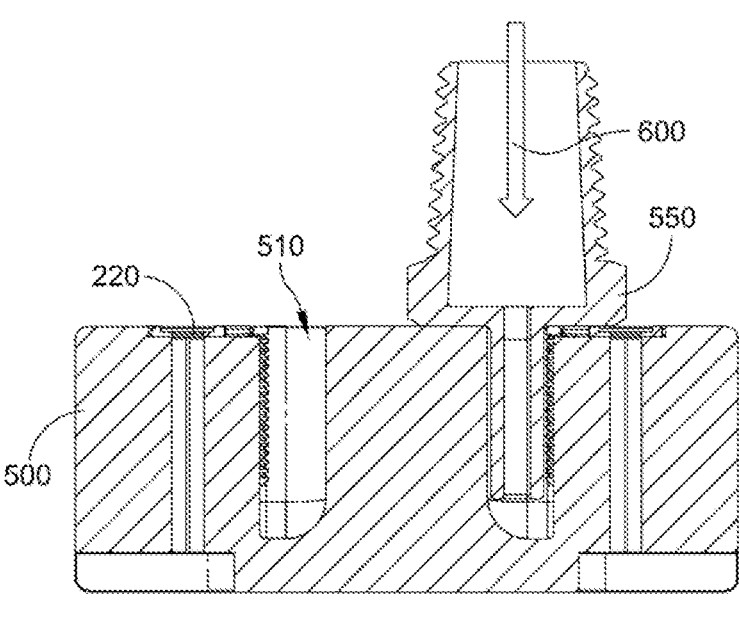
FIG. 26 is a cross-section view of the injection molding set up shown in FIG. 25.

Referring to FIGS. 25 and 26, an example of a molding process for forming the implants 200 and 300 is disclosed. A mold 500 having a plurality of mold cavities 510 is provided. Each of the mold cavity 510 is configured with the outline shape of either the implant 200 or the implant 300. A bone plate portion 220 or 320 is first placed in each of the mold cavity 510. Then, a nozzle 550 for dispensing the hydrogel material is positioned into the mold cavity 510 as shown in FIG. 26. Next, the hydrogel material, represented by the arrow 600, is dispensed into each of the mold cavity 510. Next, with each of the mold cavities 510 holding a bone plate portion 220 and filled with the hydrogel material, an appropriate post processing is carried out for cross-linking the hydrogel material to form the finished implant product 200. This process is equally applicable to the implant 300. The specifics of this post processing would be determined by the particular hydrogel material being used but would be well known to those in the art for the particular formulation of hydrogel.

Referring to FIGS. 27-37, another embodiment of an implant 400 for replacing a portion of an articulation surface of a joint is disclosed. The implant 400 comprises a main portion 410 configured for inserting into a joint and a bone plate 420 configured for securing the implant 400 to a bone that forms a joint.

Figure 30:
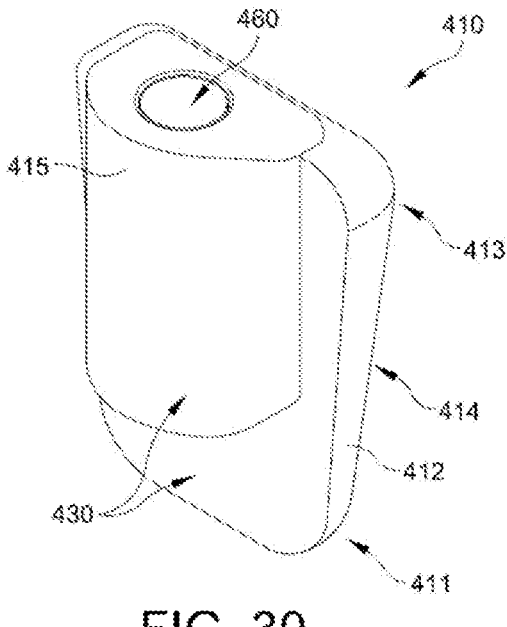
FIG. 30 is a perspective view illustration of the main portion of the hydrogel implant of FIG. 27.
Figure 31:
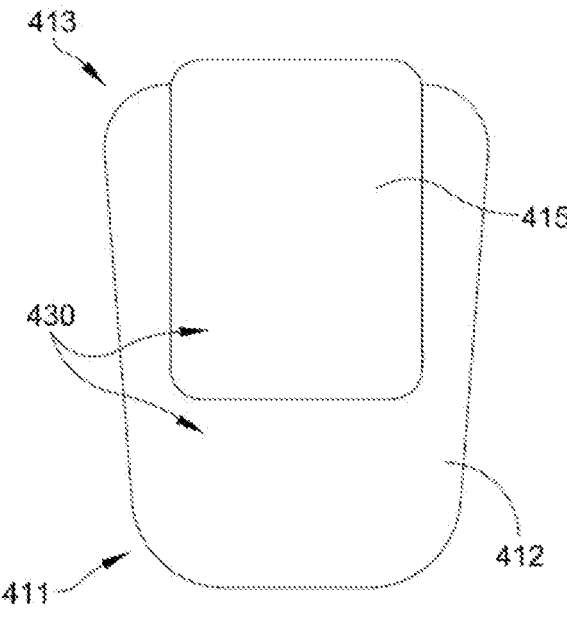
FIG. 31 is an illustration showing a view of the bone-contacting surface of the main portion shown in FIG. 30.
Figure 32:
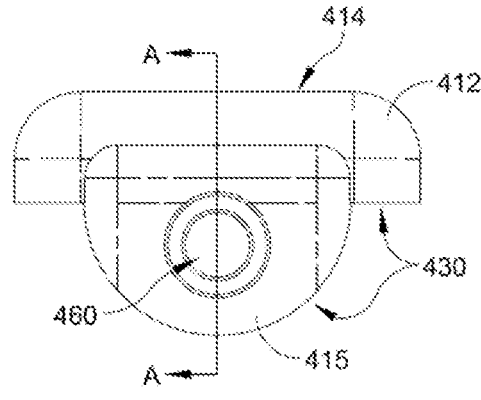
FIG. 32 is a top view illustration of the main portion shown in FIG. 31.

Referring to FIG. 30, the main portion 410 comprises a leading end 411, a trailing end 413, an articulation surface 414 and a bone-contacting surface 430 extending between the leading end and the trailing end. The leading end 411 is configured for being inserted into the joint. The main portion 410 further comprises a porous material portion 415 and a hydrogel portion 412 forming the articulation surface 414 and the bone-contacting surface 430 opposite from the articulation surface 414. The porous material portion 415 is bonded to the hydrogel portion 412 and the porous material portion 415 extends partially from the trailing end 413 towards the leading end 411 and forms a portion of the bone-contacting surface 430.

Figure 34:
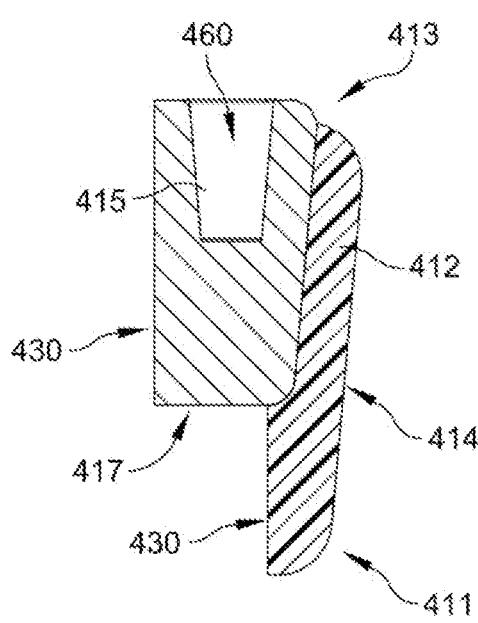
FIG. 34 is a cross-section view of the main portion shown in FIG. 31 taken through the section line A-A shown in FIG. 32.
Figure 33:
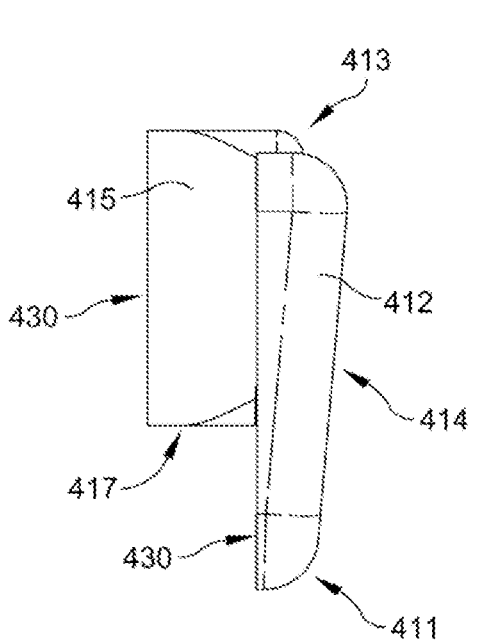
FIG. 33 is a side view illustration of the main portion shown in FIG. 31.

Referring to FIG. 30 and the cross-sectional view in FIG. 34, the porous material portion 415 comprises a tapered hole 460 at the trailing end 413.

Figure 27:
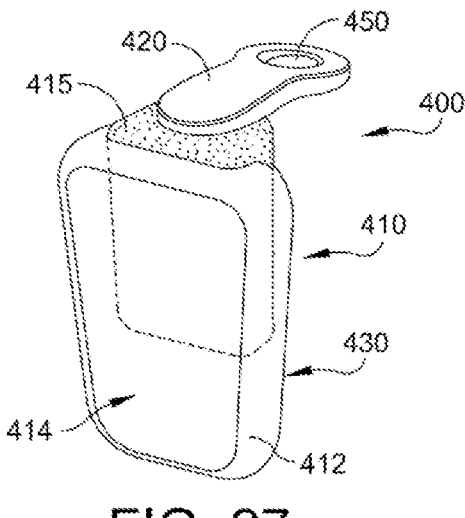
FIG. 27 is a perspective view illustration of a hydrogel implant according to a fourth embodiment.
Figures 35, 36, 37:
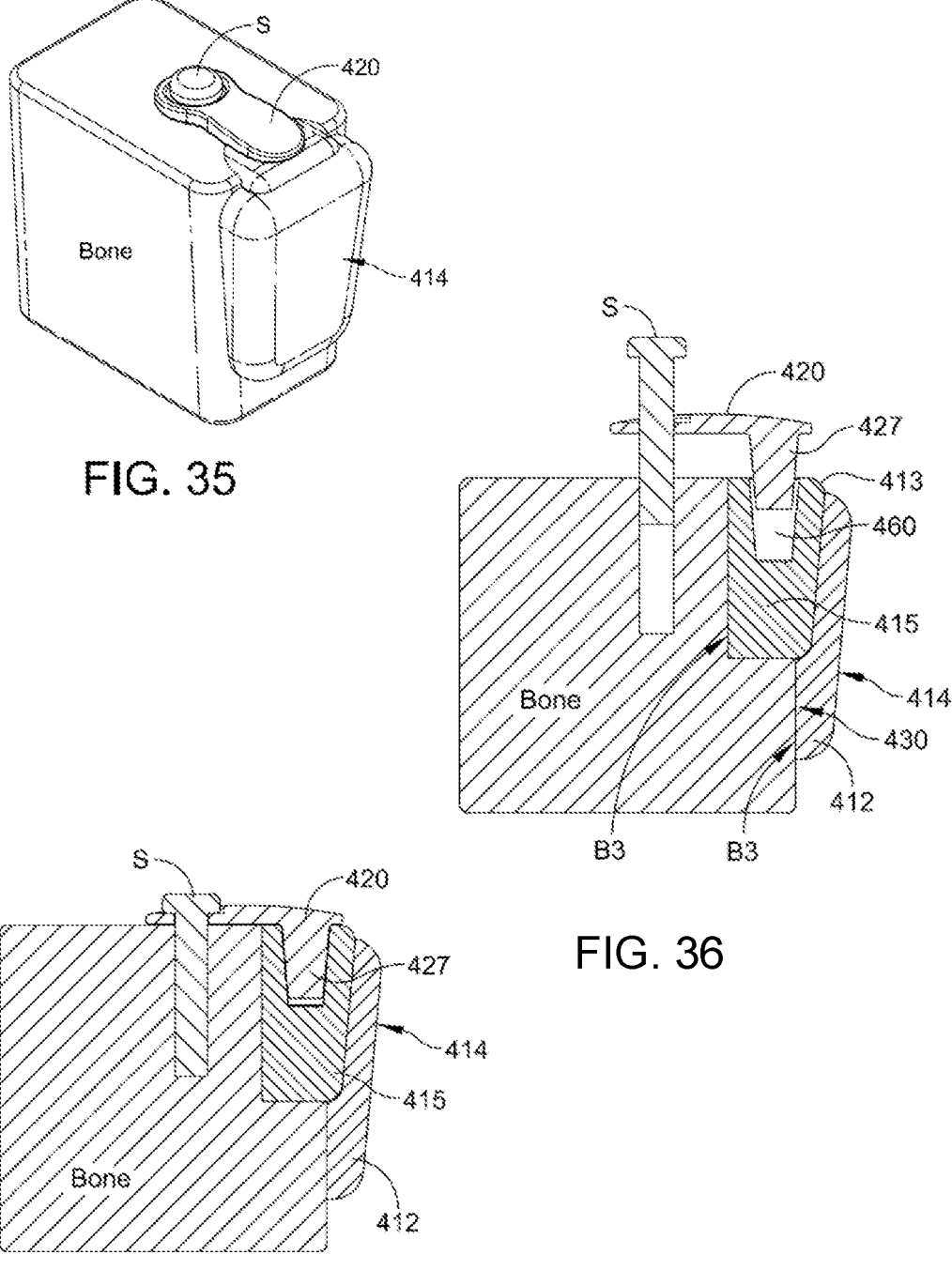
FIG. 35 is a perspective view of the hydrogel implant of FIG. 27 secured to a bone in its fully implanted configuration.
FIG. 36 is a cross-section view of the hydrogel implant shown in FIG. 35 in which the bone plate portion has not yet been seated in its fully implanted configuration.
FIG. 37 is a cross-section view of the hydrogel implant shown in FIG. 35 in which the bone plate portion is seated in its fully implanted configuration.

Referring to the cross-sectional views of FIGS. 36 and 37, in some embodiments, the bone plate 420 is formed of a solid metal and comprises a tapered stem 427 that is configured to be inserted into the tapered hole 460 in the porous material portion 415. The tapered stem 427 and the tapered hole 460 cooperate to urge the bone-contacting surface 430 of the implant 400 toward the bone when the implant 400 is inserted into the joint. Referring to FIGS. 27, 35-36, the bone plate 420 comprises at least one screw hole 450 for receiving a bone screw S.

The porous material for the porous material portion 415 can be the same material as the porous material portion 115 of the implant 100 discussed above.

In some embodiments, the hydrogel portion 412 is bonded to the porous material portion 415 by having some hydrogel material infiltrating into pores in a portion of the porous material portion. The main portion 410 comprising the hydrogel portion 412 and the porous material portion 415 can be formed by an appropriate process such as an injection molding or open cavity molding process as described above in connection with the implant embodiment 100.

FIGS. 35-37 are illustrated with the bone of a joint in which the implant 400 is secured. A portion of the bone immediately surrounding the implant 400 is illustrated conceptually as a box-like volume Bone for illustration purposes. FIGS. 36 and 37 show how the tapered stem 427 of the bone plate 420 and the tapered hole 460 of the porous material portion 415 engage each other and cooperate to urge the bone-contacting surface 430 of the implant 400 toward the bone when the implant 400 is inserted into the joint. FIG. 36 shows the implant 400 positioned in place in the Bone. The bone-contacting surfaces 430 are contacting the prepared bone surface B3. The tapered stem 427 of the bone plate 420 is partially inserted into the mating tapered hole 460 in the porous material portion 415 and a bone screw S is placed through the screw hole 450 in the bone plate 420 and starting to engage the pre-drilled hole in the Bone. FIG. 37 shows the implant 400 where the bone screw S is fully screwed into the Bone and has secured the bone plate 420 to the Bone. With the bone plate 420 in its fully-seated position, the tapered stem 427 is fully inserted into the tapered hole 460. The tapered surface of the tapered stem 427 pushes against the sidewall of the tapered hole 460 as the tapered stem 427 reaches its fully-seated position and securely holds the main portion 410 of the implant 400 in place.

Figure 28:
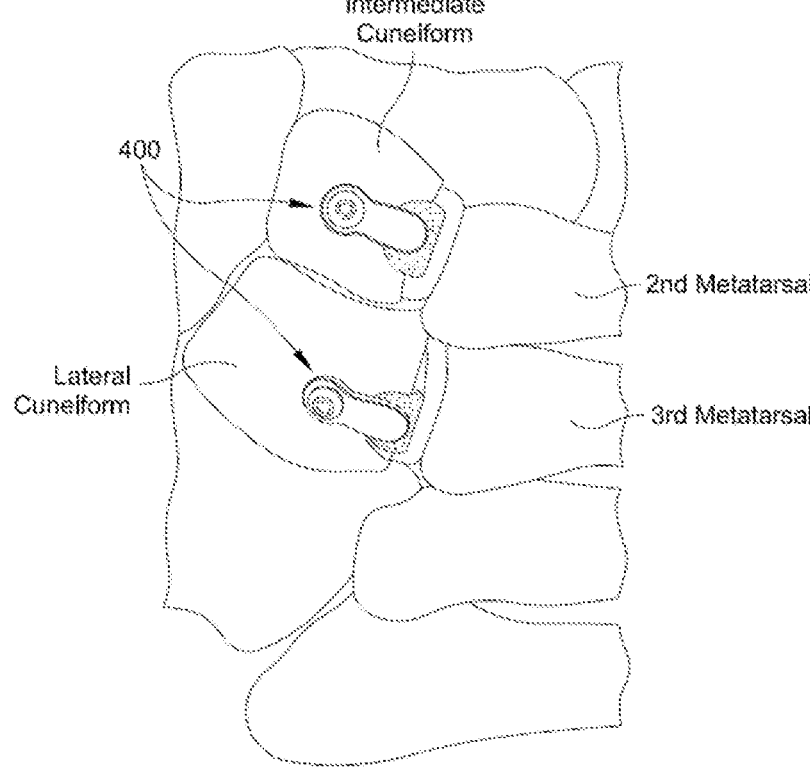
FIGS. 28-29 are illustrations showing the hydrogel implant of FIG. 27 implanted into some of the mid-foot joints.
Figure 29:
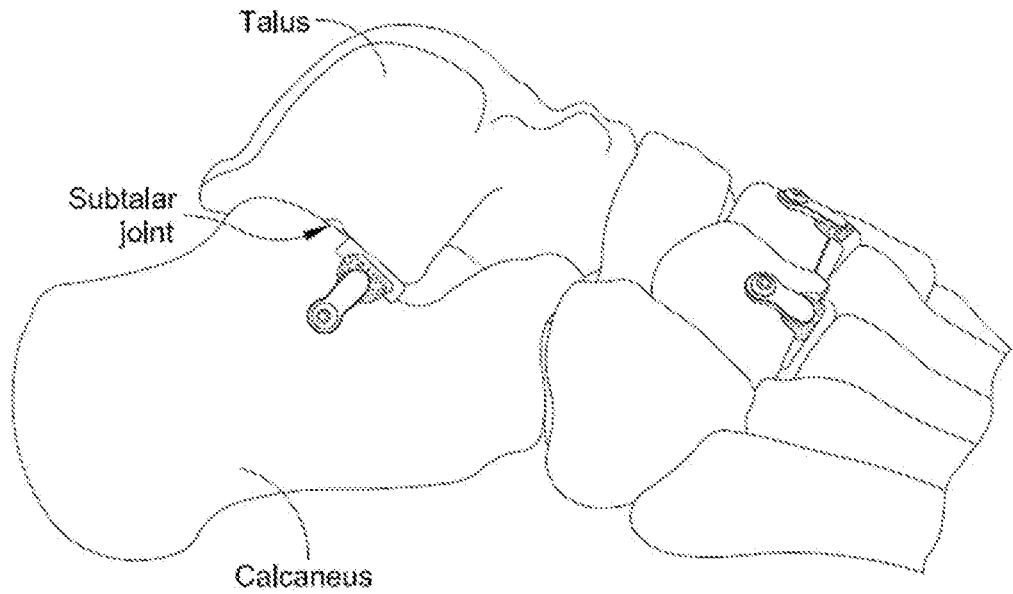

In FIGS. 28 and 29, two examples of the implant 400 are shown implanted in joint spaces between a metatarsal bone and a cuneiform bone. In FIG. 29, a third implant 400 is shown implanted in a subtalar joint space between the talus and the calcaneus.

Although the devices, kits, systems, and methods have been described in terms of exemplary embodiments, they are not limited thereto. Rather, the appended claims should be construed broadly, to include other variants and embodiments of the devices, kits, systems, and methods, which may be made by those skilled in the art without departing from the scope and range of equivalents of the devices, kits, systems, and methods.

The invention claimed is:

1. An implant for replacing a portion of an articulation surface of a joint, the implant comprising:
   a main portion configured for inserting into a joint, wherein the main portion comprises:
      a porous material portion having a first bone-engaging surface; and
      a hydrogel portion that is bonded to the porous material portion and forms an articulation surface opposite from the first bone-engaging surface; and
   a bone plate portion configured for securing the implant to a bone that forms the joint;
      wherein, the main portion has a leading end and a trailing end, wherein the leading end is configured for being inserted into the joint, and wherein the bone plate portion extends from the trailing end;
      wherein the bone plate portion has an extension piece that extends from the first bone-engaging surface and forms a second bone-engaging surface that is also formed of the same porous material as the porous material portion, and extends from the first bone-engaging surface in a direction opposite from the articulation surface at an angle with respect to the first bone-engaging surface, whereby a space is formed between the porous material portion and the extension piece at the trailing end;
      wherein the bone plate portion comprises a solid metal portion that fills the space and also forms all exterior surfaces of the bone plate portion except for the second bone-engaging surface; and
      wherein the bone plate portion has at least one screw hole for receiving a bone screw.

2. The implant of claim 1, wherein the porous material is porous metal foam.

3. The implant of claim 1, wherein the porous material is porous titanium foam.

4. The implant of claim 1, wherein the angle between the first and second bone-engaging surfaces is substantially 90°.

5. The implant of claim 1, wherein the angle between the first and second bone-engaging surfaces is an obtuse angle.

6. The implant of claim 5, wherein the obtuse angle is ≥110° and ≤160°.

7. The implant of claim 5, wherein the obtuse angle is ≥130° and ≤140°.

8. The implant of claim 1, wherein some hydrogel material from the hydrogel portion reside in some pores of the porous material portion.

9. The implant of claim 8, wherein the porous material portion is formed of porous titanium metal foam.

10. The implant of claim 1, wherein the bone plate portion and the porous material portion are formed of porous titanium metal foam.

* * * * *